United States Patent [19]

Hickey

[11] Patent Number: 4,986,916

[45] Date of Patent: Jan. 22, 1991

[54] METHOD OF MONITORING AND/OR CONTROLLING BIOLOGICALLY CATALYZED REACTIONS

[75] Inventor: Robert F. Hickey, Haydenville, Mass.

[73] Assignee: New York State Energy Research and Development Authority, Albany, N.Y.

[21] Appl. No.: 145,774

[22] Filed: Jan. 19, 1988

[51] Int. Cl.$^5$ .............................................. C02F 3/12
[52] U.S. Cl. ..................................... 210/603; 210/614; 210/96.1
[58] Field of Search ................... 210/603, 85, 614, 86, 210/709, 87, 96.1; 55/68

[56] References Cited

U.S. PATENT DOCUMENTS

| | | | |
|---|---|---|---|
| 3,926,737 | 12/1975 | Wilson et al. | 195/108 |
| 3,926,738 | 12/1975 | Wilson et al. | 195/127 |
| 4,349,435 | 9/1982 | Ochiai | 210/96.1 |
| 4,437,992 | 3/1984 | Saito et al. | 210/603 |
| 4,681,612 | 7/1987 | O'Brien et al. | 55/68 X |
| 4,690,755 | 9/1987 | Friedman et al. | 210/96.1 |

OTHER PUBLICATIONS

Conrad et al., "Carbon Monoxide Production by *Methanobacterium thermoautotrophicum*", from Microbiology Letters, 1983.
Hickey et al., "Production of Trace Levels of Carbon Monoxide during Methanogenesis on Acetate and Methanol", Biotechnology Letters, 1-1987, vol. 9, pp. 63-66.
O'Brien et al., "Association of Hydrogen Metabolism with Unitrophic . . . on Carbon Monoxide", Journal of Bacteriology, 4-1984, pp. 373-375.
Krzycki et al., "Acetate Catabolism by *Methanosarcina barkeri* . . . and Methylreductase", Journal of Bacteriology, 9-1985, pp. 1000-1006.
Bott et al., "Coupling of Carbon Monoxide Oxidation to $CO_2$ and $H_2$ . . . *barkeri*", Eur. J. Biochem, 1986, 159, 393-398.
Elkmanns et al., "Formation of carbon monoxide from $CO_2$ and $H_2$ by *Methanobacterium thermoautotrophicum*", Eur. J. Biochem., 1985, 146, 149.
Nelson et al., "Carbon Monoxide-Dependent Methyl Coenzyme M Methylreductase in Acetotrophic Methosarcina spp.", J. of Bacteriology, 11/1984, pp. 526-532.
Bott et al., "Defective Formation and/or Utilization of Carbon Monoxide . . . on Acetate as Carbon Source", Arch. Microbiol., (1985), 143:266-269.
Kohler et al., "Carbon Monoxide Dehydrogenase and Acetate Thiolinase in *Methanothrix soehngenii*", FEMS Microbiology Letters, 1984, 21, 287-292.
Eikmanns et al., "Catalysis of an Isotopic Exchange between . . . by *Methanosarcina barkeri* grown on acetate", Archives of Microbiology, 1984, pp. 365-370.

*Primary Examiner*—Frank Spear
*Attorney, Agent, or Firm*—Heslin & Rothenberg

[57] ABSTRACT

In a method of monitoring and/or controlling a biologically catalyzed reaction, a trace gas which either is, or equilibrates with a metabolic intermediate is identified, and the concentration of the trace gas evolving from the reaction is measured. The measured concentration of trace gas is employed to evaluate the metabolic status of the reaction by a deterministic relationshhip, e.g. an empirical relationship or thermodynamic model. The deterministic relationship may involve other gaseous parameters of the reaction. Preferably, the measured concentration of the trace gas is converted via the deterministic relationship into an estimate of the concentration of a different chemical component of interest for a particular application of the reaction. Carbon monoxide has been found to be a suitable trace gas for purposes of monitoring the metabolic state of the anaerobic digestion process. Metabolic state information derived on-line in accordance with the present invention can be advantageously used to control the reaction.

20 Claims, 7 Drawing Sheets

METHOD OF MONITORING AND/OR CONTROLLING BIOLOGICALLY CATALYZED REACTIONS

BACKGROUND OF THE INVENTION

1. Field of the Invention

This invention relates generally to biologically catalyzed processes which can occur in man-made environments or natural ecosystems and, more particularly, to a method for monitoring and controlling the condition of such processes as anaerobic digestion.

2. Background Art

Anaerobic digestion is a biologically catalyzed process in which organic matter is decomposed, in the absence of oxygen, primarily to the gaseous end products of carbon dioxide and methane. Naturally occurring habitats for the unique consortium of microbes that carries out this sequence of fermentative reactions include marshes, rice paddies, benthic deposits and ruminants (such as cattle, sheep and buffalo). Anaerobic digestion is well known to sanitary engineers and has been used for sludge treatment at wastewater treatment plants for over 100 years. The primary purpose of the process has been for sludge digestion to achieve waste stabilization and solids reduction. Over the recent past it has also been applied for the treatment of both liquid industrial and municipal wastewaters.

Due to the inherent slow growth rate of the methane producing bacteria, conventional anaerobic digesters are sensitive to changes in hydraulic loading, organic loading and temperature, and recover slowly once they are upset. Advances in reactor technology (i.e., fixed film systems) have effectively eliminated the problem of hydraulic overloading for industrial wastewater treatment. Upsets as a consequence of organic overloading or inadvertent toxicant induced inhibition still are potential problem areas. The last remaining hurdle to widespread application of anaerobic treatment to industrial wastewaters is improved process reliability.

Unfortunately, despite the great strides that have been made toward increasing the fundamental understanding of how anaerobic systems function during the past fifteen years, little of this information has been integrated into process control strategies and testing procedures. The same analyses and process control techniques developed almost two decades ago are still utilized today.

Ideal indicators should be capable of measuring the progress of sludge digestion and signal impending upsets before they occur. Several of the more commonly used indicators include: (1) volatile acids to alkalinity ratio; (2) gas production rates and gas composition; (3) pH; and (4) volatile solids reduction (digester efficiency). None of these can accurately indicate the condition of the digestion process singly. Several of these indicators are usually considered together to properly control the process.

Although these indicators are useful for monitoring gradual changes, they do not directly reflect the current metabolic status of the active organisms in the digester. These common indicators are useful for detecting process upsets once they are underway. In many instances this may be adequate to avoid system failure for slow to develop difficulties such as a gradual organic or hydraulic overload.

More rapid monitoring techniques are needed, however, to avoid significant process deterioration and possible failure, especially for systems with relatively short hydraulic residence times (HRT) such as the various fixed-film reactor configurations and anaerobic contact processes.

There have been efforts to develop better control strategies—mostly relating digester performance with parameters associated with metabolic activity such as enzyme activity levels, and specific electron carriers. These newer techniques include acid and alkaline phosphotase activity, dehydrogenase activity, adenosin triphosphate activity and factor 420 levels.

All of the above attempts have met with limited success. They require rather sophisticated and time consuming wet chemical techniques that do not lend themselves to on-line measurement. Conclusive evidence that any of these approaches, even if practical assay techniques suitable for on-line measurement can be developed, can accurately function as acceptable indicators has not been demonstrated.

Analyzing parameters in the gaseous headspace offers several distinct advantages over liquid or slurry phase monitoring. First, process instrumentation in the field of gas chromatography and related fields has advanced much more quickly than its liquid counterpart. Second, the gas phase of an anaerobic treatment system of any type, is considerably more amenable to on-line monitoring than the liquid phase. Sampling conditions are much less severe with respect to the potential for chemical or physical fouling.

Analysis of the gas phase of anaerobic systems is, in fact, a vital part of current process control strategies. Monitoring has been, however, confined to the primary gaseous components, methane and carbon dioxide. No insight into the current metabolic status of the organisms involved is obtained from monitoring these two gaseous products. There has been, however, at least one anaerobic process control system proposed based on, in part, measuring, methane. Ochiai (U.S. Pat. No. 4,349,435) proposed controlling anaerobic treatment systems based on performing mass balances of oxygen demand (OD) in the influent, effluent and the equivalent OD leaving as methane gas. The admitted deficiency of not being able to reliably measure the oxygen demand of liquid samples severely limits this approach.

The use of monitoring trace gases that are somehow linked to the metabolic status of the major biochemical process occurring has been proposed by Saito et al. (U.S. Pat. No. 4,437,992), who describe a control system for activated sludge based upon measuring, among other parameters, $N_2O$, a reported metabolic intermediate in nitrogen conversion. However, the exact nature of the relationship of $N_2O$ to the process is unclear from the teaching of Saito et al. and the patent is specific for the aerobic activated sludge process.

It has been suggested that there is the potential to obtain some measure of the metabolic status of anaerobic systems by monitoring the concentration of an intermediate product, hydrogen, which is present at trace levels in well-functioning treatment systems. This is based upon the fact that hydrogen is the direct precursor of approximately 30 percent of the methane produced in anaerobic digesters and industrial waste systems.

The patent of Friedman et al. (U.S. Pat. No. 4,690,755) makes mention of using hydrogen as a control parameter. Hydrogen, in this context, represents the product of one biochemical reaction and is the substrate of a sequential reaction that combines hydrogen with carbon dioxide to form methane. Accordingly, hydrogen is, in this case, an intermediate product and not a metabolic intermediate within a biochemical reaction as in $N_2O$.

It is recognized that approximately 70 percent of the methane formed in these anaerobic treatment systems is formed from conversion of acetate to methane and carbon dioxide via the reaction below:

$$CH_3COO^- + H^+ \rightarrow CH_4 + CO_2 \quad (1)$$

Monitoring strategies based on measuring hydrogen gas only, do not yield any information concerning this important biochemical reaction. This represents a severe limitation since acetate conversion to methane is believed to be the most sensitive and rate limiting step for methanogenesis.

A need thus exists for a new process monitoring approach capable of providing on-line, a rapid, reliable and accurate indication of the metabolic status of anaerobic digestion and other biologically catalyzed processes.

SUMMARY OF THE INVENTION

In accordance with the present invention, this need is satisfied and the deficiencies of the prior art overcome, by a monitoring method in which: a trace gas is identified which either is, or equilibrates with a metabolic intermediate of the particular biologically catalyzed reaction; the concentration of the trace gas evolving from the reaction is measured; and its measured concentration is employed to evaluate the metabolic status of the reaction via a deterministic relationship, e.g. an empirical relationship or thermodynamic model. The thus derived metabolic state information can be advantageously used to control the reaction.

In accordance with one aspect of the invention, the measured concentration of the trace gas is converted via the deterministic relationship into an estimate of the concentration of a different chemical component of interest for a particular application of the reaction. The different chemical component can be a reactant, metabolite, or product of the reaction which bears a known relationship to the reaction's metabolic status.

In accordance with another aspect of the invention, a sample of gases evolving from the reaction is collected, and conditioned to remove moisture and particulate matter therefrom. The concentration of the trace gas in the sample is then measured. The concentration of other gases (or other parameters) may also be measured and employed in the deterministic relationship.

In a further aspect of the invention, information as to the metabolic status of an anaerobic digestion process involving an acetate to methane reaction is gained by monitoring a specific trace gas, carbon monoxide, that is a metabolic intermediate and/or equilibrates with a metabolic intermediate of the acetate conversion pathway. The present invention is characterized by monitoring the concentration of this key gaseous parameter, carbon monoxide, either singly or in concert with additional gaseous parameters, such as hydrogen, carbon dioxide and methane, and developing relationships that allow estimation of the acetate concentration of the system to be made. The nature of these relationships can be purely empirical or developed from a scientifically based foundation or understanding of the reactions occurring, e.g. a thermodynamic model. Such relationships are referred to herein as deterministic relationships.

One of the major advantages of the invention is that the analyses are relatively simple and readily amenable to on-line data acquisition so that information which heretofore was relatively difficult to obtain even on a periodic basis, can be conveniently acquired in a near continuous mode. This is especially advantageous for monitoring anaerobic processes that may be subject to rapid changes and that may require some type of on-line monitoring and/or control to assure process stability or improved efficiency. The information obtained via the monitoring of CO with respect to the methanogenic reaction (or other trace gases for other biologically catalyzed processes) can be used to automatically generate a signal that, in turn, can be used to control a process variable such as liquid or sludge feed rate in a wastewater treatment facility.

Accordingly, a principle object of the present invention is to provide a new, sensitive and practical method of monitoring biologically catalyzed reactions, e.g. anaerobic digestion, which affords a rapid, accurate indication of the metabolic status of the reaction.

Another object of the invention is to improve the reliability of controlled biologically catalyzed processes.

A further object is to provide a method for monitoring biologically catalyzed processes which is capable of application to a wide variety of processes occurring in natural ecosystems and engineered systems.

A still further object is to provide process control strategies and testing procedures for biologically catalyzed reactions which apply an empirically derived and/or scientifically based understanding of the reactions occurring.

Yet another object is to provide an early indicator of the progress of anaerobic sludge digestion which is capable of monitoring both gradual and rapid changes in the metabolic state of the active organisms, which lends itself to on-line use, and can be readily implemented with available equipment.

BRIEF DESCRIPTION OF THE DRAWINGS

These and other objects, features and advantages of the present invention will be more readily understood from the following detailed description when read in conjunction with the accompanying drawings in which.

DETAILED DESCRIPTION OF THE INVENTION

The present invention will now be described, by way of example, in terms of its application to anaerobic digestion. Those skilled in this art will, however, appreciate that the invention is also applicable to other biologically catalyzed processes.

Figure 1:
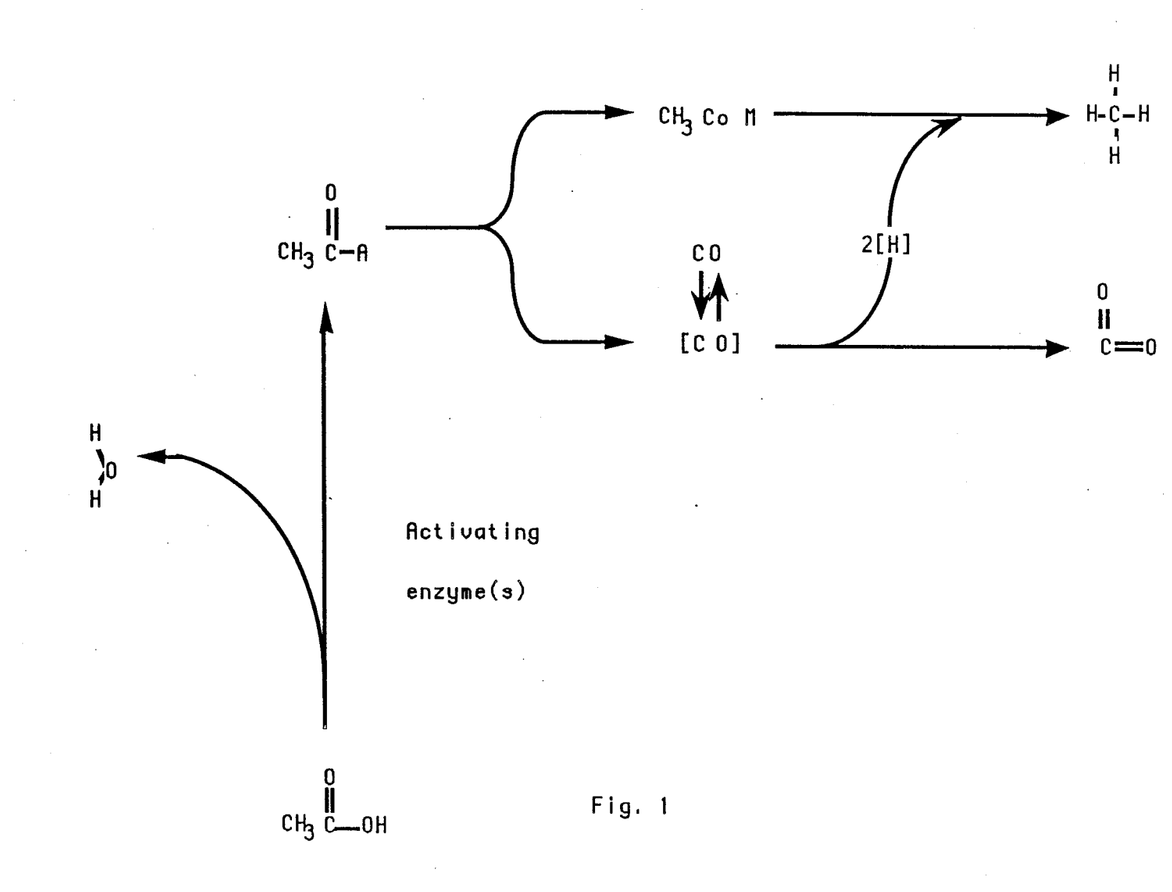
FIG. 1 is a schematic representation of some of the key enzymatic reactions that occur during the biologically catalyzed conversion of acetate to methane and carbon dioxide.

The conversion of acetate to methane is quantitatively the most significant step in the anaerobic conversion of organic matter in both engineered wastewater treatment systems and natural environmental ecosystems. Approximately 70 percent of the methane produced is formed via conversion of acetate to methane. Without this final step, therefore, little in the way of reduction in oxygen demand or production of a valuable resource, methane gas, is accomplished. This biochemical reaction is actually a sequence of steps. Although all of the steps have not yet been completely defined, a reasonably clear picture of what occurs has been elucidated. FIG. 1 shows that acetate is first bound to a carrier in an activated form (believed to be acetyl-CoA or acetyl-P). This activated form of acetate is subsequently split into a bound methyl group and a bound carbonyl (CO) group. The methyl group is further reduced to methane ($CH_4$) in conjunction with the coupled reaction of anaerobic oxidation of the bound CO to $CO_2$. This latter reaction supplies the necessary reducing power, represented by 2(H), to allow the reduction of methyl-CoM to methane. FIG. 1 also shows the hypothesis that the bound CO ([CO]) equilibrates with gaseous CO. As is discussed below, it was this possibility that lead to the experimental work that resulted in the present invention.

Acetate catabolising methanogens have extremely high levels of carbon monoxide dehydrogenase enzyme (CO-DH) activity. The production of trace levels of CO has been observed in other organisms possessing CO-DH enzyme activity, presumably due to equilibration of a bound CO compound with gaseous CO.

It was the possibility that trace amounts of CO might be evolved during the catabolism of acetate and that the concentration of CO could be related to the concentration of acetate and, therefore, provide a convenient and rapidly responding surrogate measure of acetate for engineered wastewater treatment and natural ecosystems that prompted this work.

Figure 2:
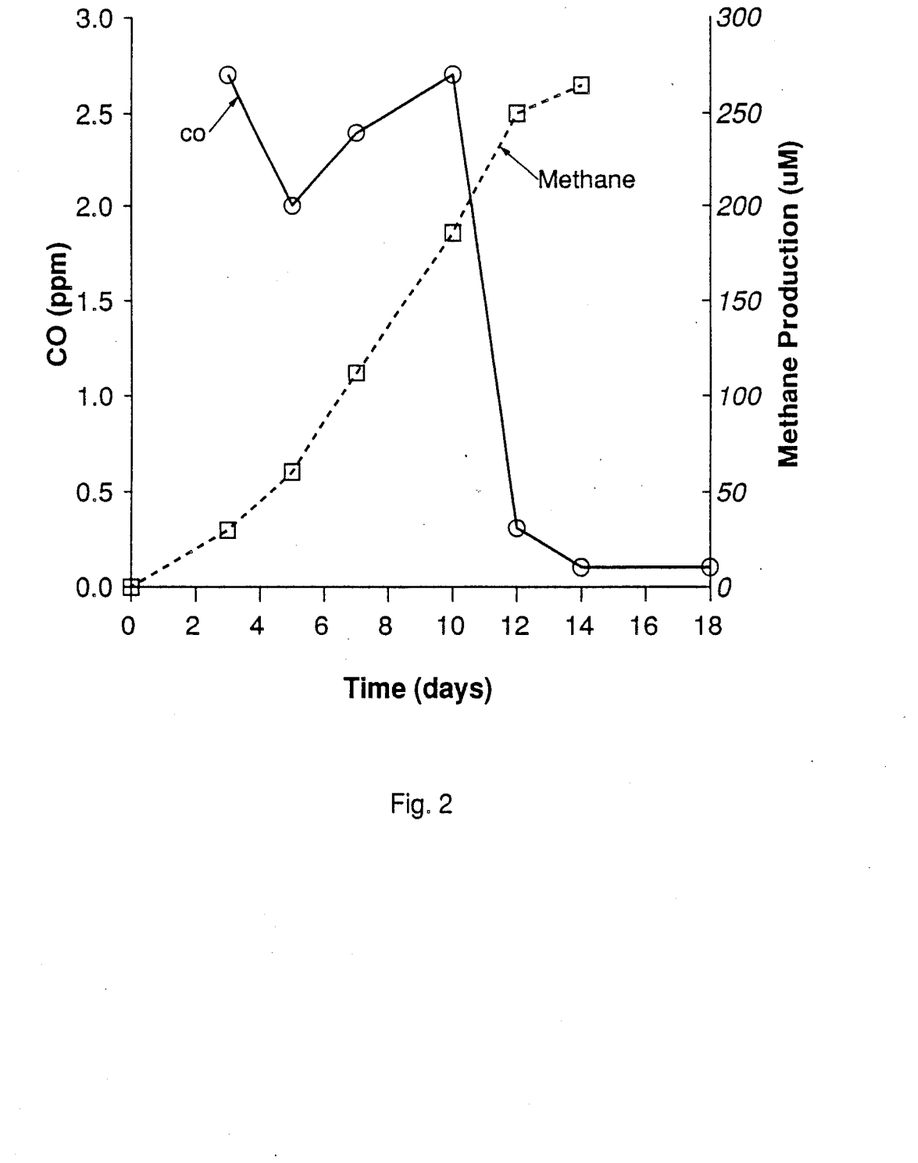
FIG. 2 is a plot of data showing the evolution over time of carbon monoxide during the methanogenic process illustrated in FIG. 1.

Initially, the gaseous headspace of several laboratory anaerobic digesters were monitored and observed to contain approximately 300-400 parts per billion, (ppb), on a volume per volume basis, of CO. A pure culture of a strain of one of the two known acetate catabolising methanogens, *Methanosarcina barkeri*, strain 227 was examined to determine if CO was in fact evolved during methanogenesis from acetate. FIG. 2 shows the progress of a batch fermentation of a methanogen (*Methanosarcina barkeri* strain 227) converting acetate to methane and carbon dioxide. The open circles connected by the solid line are measured concentrations of CO and the open squares connected by the dotted line represent the cumulative production of methane gas during the fermentation. At time zero, the headspace above the culture was purged and replaced with a gas containing nitrogen and carbon dioxide (70:30 by volume) and low CO (500 ppb). By the first sample time, the CO concentration had risen to over 2500 ppb (2.5 ppm) demonstrating that CO is indeed evolved during the conversion (catabolism) of acetate to methane and carbon dioxide.

The next step was to evaluate if in fact gaseous CO levels were somehow related to the concentration of acetate. The fact that CO is related to acetate concentration is shown in the following example

EXAMPLE 1

The effect of increasing the organic loading to an anaerobic sludge digester was simulated by feeding waste activated sludge (WAS) at 1, 2. and 3 times the normal solids concentration (1.25 percent total solids) to a 10 day hydraulic residence time (HRT) digester inoculum that was acclimated to digesting WAS. The assay, which was conducted for 24 hours at 35° C., was designed to mimic a typical daily draw and fill operation employed at many wastewater treatment plants. Table 1 presents test data for cumulative methane production, composition of major and minor gaseous products of interest and accumulated acetate at the conclusion of the assay.

TABLE 1

Concentrations of Acetate and Selected Headspace Gases Produced as a Result of Batch Anaerobic Digestion of Waste Activated Sludge at Various Applied Organic Loadings.

| Organic Loading Rate (gVS/ 1-day) | $CH_4$ Prod (uM) | $CH_4$ (atm) | $CO_2$ (atm) | $H_2$ (ppm) | CO (ppb) | Acetate (mM) |
|---|---|---|---|---|---|---|
| 1.0 | 673 | 0.232 | 0.293 | 72 | 1220 | 2.0 |
| 2.0 | 716 | 0.242 | 0.321 | 72 | 1465 | 4.6 |
| 3.0 | 754 | 0.249 | 0.339 | 76 | 2060 | 7.0 |

Increased loading resulted in a build up of volatile acids and greater headspace concentrations of CO. This supports the hypothesis that acetate and CO concentrations are related in digester type systems.

The direct and rapid nature of the relationship between CO and acetate concentration is the subject of example 2.

EXAMPLE 2

Figure 3:
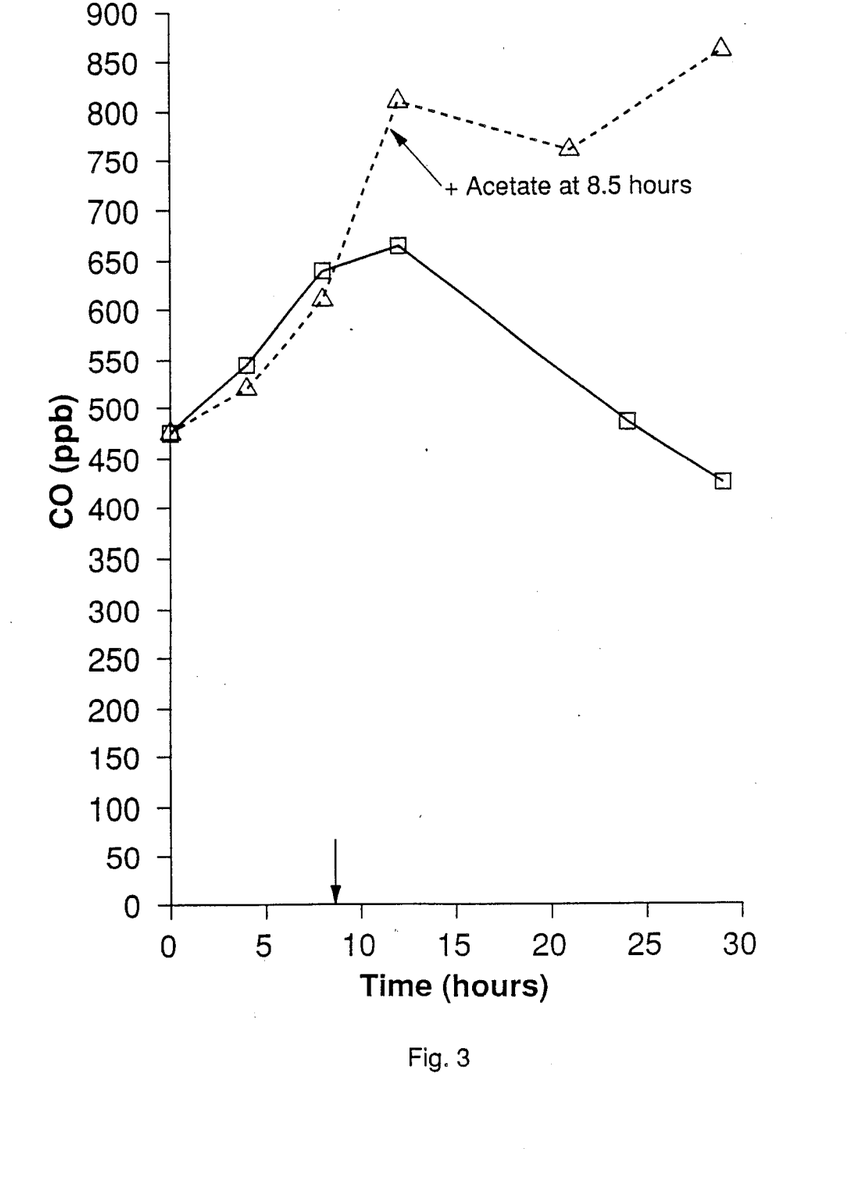
FIG. 3 is a plot of data that illustrates the rapid response of CO in the gaseous headspace of an anaerobic digester to an increase in the level of dissolved acetate.

This example is best explained with reference to FIG. 3. In FIG. 3, squares connected by the solid line represent the measured concentrations of CO of control samples (duplicate) while the triangles connected by the dotted line represent a sample to which a pulse of acetate (10 mM) was added at 8.5 hours. All samples were prepared as in example 1, except in this case a 20-day HRT inoculum was used, and handled in exactly the same fashion up until the addition of the acetate pulse. Subsequent to the addition of acetate (indicated by the arrow on the abcissa of the graph), which increased the acetate concentration, the gaseous CO concentration rose sharply to a level well above that measured in control samples. This demonstrates the direct correlation between acetate concentration and CO and further shows the relatively rapid nature of the response.

EXAMPLE 3

Figure 4A:
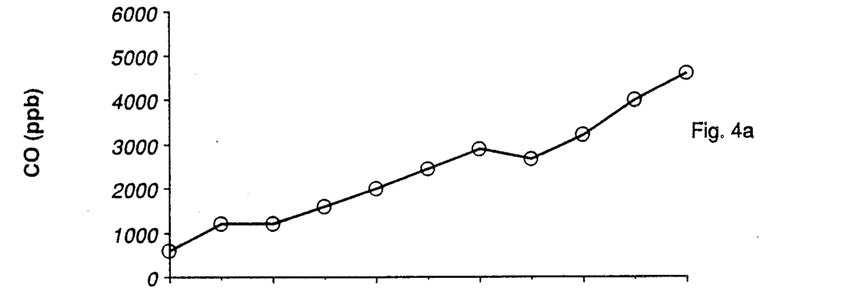
FIG. 4 is a set of graphs showing the daily values of (a) measured gaseous CO concentrations, (b) measured acetate concentrations, and (c) calculated acetate concentrations derived from the measured gaseous CO concentrations via a regression equation.
Figure 4B:
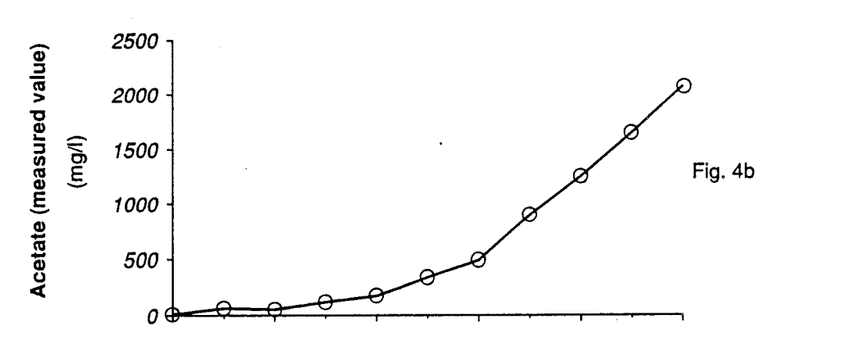
Figure 4C:
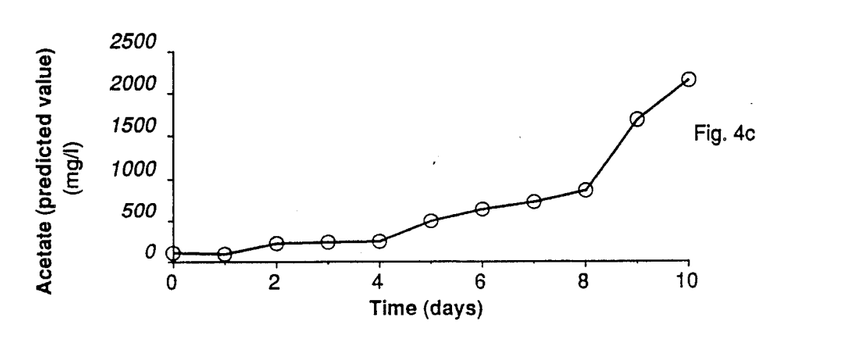

The correlation of CO, measured on a daily basis, to the acetate concentrations measured on a digester system experiencing operational problems due to an organic overload, is the subject of this example. This experiment was conducted using WAS as the feedstock for a 5-liter anaerobic digester maintained at 35° C. and operated in a daily draw and fill mode. The data presented in FIG. 4 is information generated from sampling the digester at the conclusion of each 24 hour cycle. The digester was maintained completely mixed by recirculation of the liquid contents of the digester with a varistaltic type tubing pump operated at approximately 3 liters per minute. As can be seen, by comparing FIGS. 4a and 4b, the concentration of gaseous CO rose in response to a build-up of acetate. It was observed in other experiments (not shown) that in addition to acetate, the concentration of $H_2$ also influenced the observed level of CO. It was further discovered that the correlation between CO and acetate could be improved if the acetate concentration was correlated to the ratio of CO and $H_2$ gas (FIG. 4c) according to the fitted regression of the form:

$$\text{Acetate} = A * \left(\frac{CO}{H_2}\right)^b \quad (2)$$

where
Acetate=mg/L
CO=parts per billion (ppb)
$H_2$=parts per million (ppm)
A,b=fitted regression coefficients FIG. 4 shows the daily values of (a) measued gaseous CO concentrations, (b) measured acetate concentrations and (c) calculated acetate concentrations derived from the regression equation presented as equation (2), obtained from a digester system experiencing operational problems due to an organic overload.

The values of A and b, calculated from the data set presented in FIG. 4c, were 0.386 and 1.76, respectively.

Figure 5:
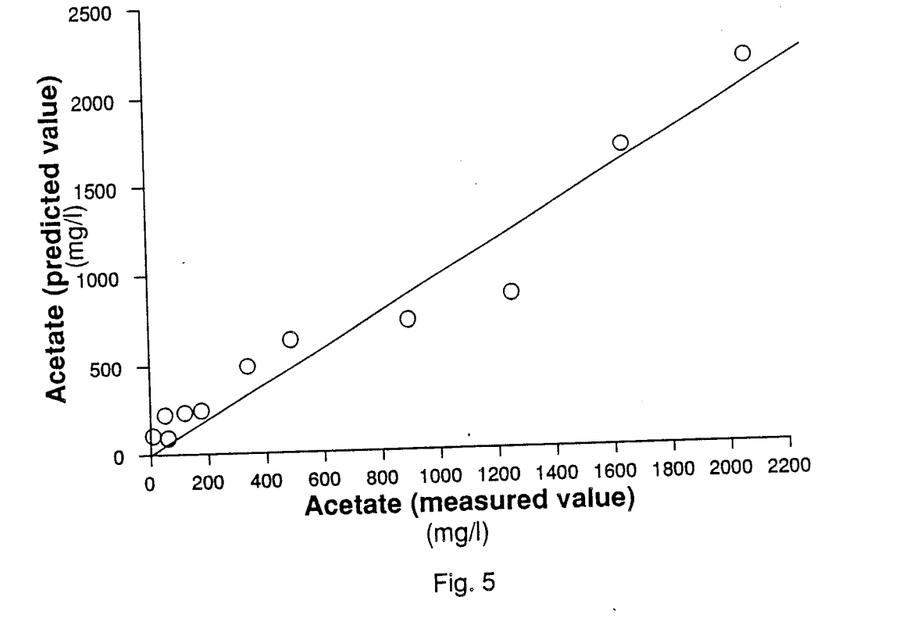
FIG. 5 is a bivariate plot that compares predicted acetate concentration and measured acetate concentration.

FIG. 5 is a bivariate plot that compares predicted acetate concentration (based on the regression presented as equation (2)) and the measured acetate concentration. The line in the plot represents the line of equal value (i.e. predicted acetate concentration equals measured acetate concentration). As can be seen in this bivariate plot, this regression appears to work well at the higher concentrations of acetate and CO (where this information is most crucial) and less well at lower concentrations for accurately predicting acetate. It should be noted that for the case presented, the concentrations of the major gaseous products, $CH_4$ and $CO_2$, remained relatively constant. Application of the simple regression of equation (2) to a system where the headspace methane content was initially at zero and then allowed to increase did not predict the actual acetate concentration very well. A further refinement, presented in example 4, can be made that will allow these type cases (variable methane and/or carbon dioxide concentrations) to be monitored. Development of this relationship is presented below.

This is the most sophisticated of the relationships between CO and acetate and is based upon a thermodynamic evaluation of the conversion of acetate to methane and carbon dioxide. For the purposes of thermodynamically evaluating the role of CO in acetate catabolism, the reaction (equation (1)) can be rewritten as two half cell reactions (equations (3) and (4)).

$$CH_3COO^- + 3H^+ + 2e^- \rightarrow CH_4 + CO + H_2O \quad (3)$$

$$CO + H_2O \rightarrow CO_2 + 2e^- + 2H^+ \quad (4)$$

where $e^-$ represents the charge associated with electrons or electron equivalents.

Further, assuming the electron carriers involved in the coupling of these two reactions are in equilibrium with the $H_2/H^+$ couple, yields the two equations presented below, along with the free energy, (expressed as Kilojoules), for each half reaction.

| | Free Energy $\Delta G^{o'}$ (KJ/reaction) |
|---|---|
| $CH_3COO^- + H_2 + H^+ \rightarrow CH_4 + CO + H_2O$ | −15.8 (5) |
| $CO + H_2O \rightarrow CO_2 + H_2$ | −20 (6) |

Using information generated in a series of experiments allowed estimation of the actual free energies associated with each of the half-reactions presented above. It was observed that the relative fraction of energy available to each half reaction remained constant despite changes in the overall amount of energy available for conversion of acetate to methane and carbon dioxide. Approximately 54 percent of the energy was found to be associated with equation (6) while the remaining 46 percent is associated with equation (5). Using this and substituting into the Nerst form of equations (5) and (6) permits development of equation (7) which allows an equilibrium acetate value to be calculated based upon only the gaseous parameters measured. This equation is:

$$\text{Acetate} = 0.137 * \left(\frac{CO}{H_2}\right)^{1.85} * [(CH_4)/(CO_2)^{0.85}] \quad (7)$$

where: Acetate = mg/L  $CO_2$ = atmospheres
CO = ppb  $CH_4$ = atmospheres
$H_2$ = ppm A more general form of this equation that allows differing relative energy for each half reaction to be used is presented in equation (8).

$$\text{Acetate} = C * \left(\frac{CO}{H_2}\right)^{d+1} * [(CH_4)/(CO_2)^d] \quad (8)$$

where $$d = \frac{\text{fraction of energy for eq. (5)}}{\text{fraction of energy for eq. (6)}}$$

It is evident that for a system with essentially constant concentrations of methane and $CO_2$, that this relationship effectively reduces to approximately the regression presented earlier (equation (2)), i.e. the form of the equation will remain the same but the values of the coefficients may vary somewhat depending upon the concentrations of methane and carbon dioxide. Under normal circumstances, it may be sufficient to monitor the $CO/H_2$ ratio for anaerobic systems that experience a relatively constant concentration of gaseous $CH_4$ and $C0_2$. This could include monitoring of continuously operated anaerobic digesters and/or industrial wastewater treatment systems. Other systems or natural environments subject to appreciable variation in the concentrations of methane and/or $CO_2$ will in most cases require use of the thermodynamic relationship presented in equation (7).

Application of the thermodynamic based relationship in an on-line data acquisition mode is presented in Example 4.

EXAMPLE 4

In this experiment, information was collected on a 15-minute interval basis from a digester subject to organic overloading. A 5-liter test digester operated in a daily draw and fill mode, was used in conjunction with an on-line data acquisition system that allowed 15-minute interval sampling of gas production rate, and quantification of headspace methane, carbon dioxide, hydrogen and carbon monoxide. Methane and carbon dioxide were quantified with a dual Infra Red analyzer and a RGD2 mercury oxide based reduced gas chromatographic system was used to quantify trace levels of hydrogen and carbon monoxide.

Figure 6:
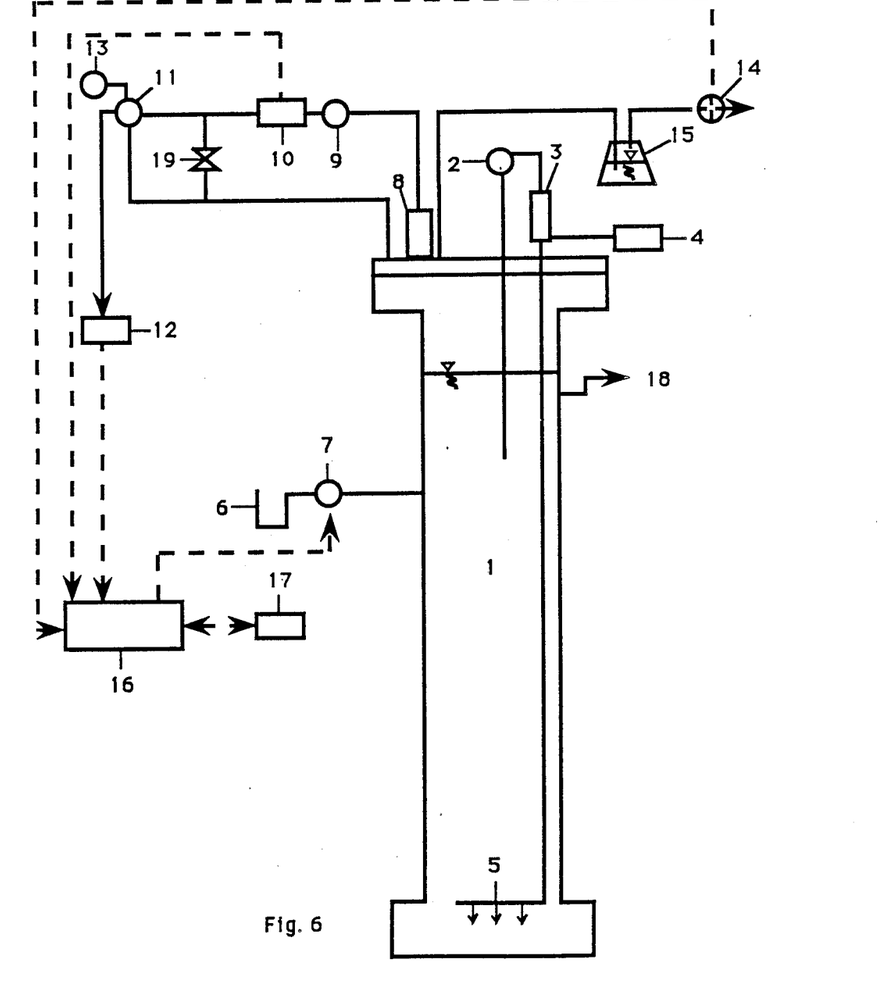
FIG. 6 is a schematic representation of a laboratory test digester used to monitor CO and other gases in a real-time, on-line mode, and also illustrates how the monitored results might be used to control the digestion process.

FIG. 6 is a schematic representation of the 5-liter laboratory test digester used to conduct the experiments. The contents of the digester 1 are mixed by a pump 2 that withdraws the sludge from the top of the digester and returns it to the bottom of the digester through a flow distribution system 5. The pH of the system can be monitored by a pH probe 3 coupled to a recorder 4. Influent (feed) sludge is forwarded to the reactor via a pump 7 from a feed reservoir 6. Effluent is discharged from conduit 18.

The gas measurement system consists of a filter/water trap 8 used to condition the gas so as to avoid operational problems in the gas measuring devices due to particulates and condensed water vapor. The gas is withdrawn from the reactor headspace with a diaphram pump 9 at a flow rate of approximately 300 ml/min and forwarded through a dual Infra Red (IR) analyzer 10 that sequentially measured carbon dioxide and methane. Upon exit from the IR unit, a 20 to 30 ml/minute side stream is directed through a 0.1 ml sample loop on an automatically controlled sampling valve 11 by throttling valve 19. At a predetermined time interval the sampling valve is positioned to send the 0.1 ml sample to the chromatographic system 12 that quantifies the concentration of CO and hydrogen. The sample is carried to the chromatograph by a carrier gas 13. Gas produced by the anaerobic fermentation is measured by a totalizer 14 after flowing through a liquid trap 15 designed to prevent contamination of the reactor headspace with atmospheric gases. Signals from the gas totalizer, and concentration measurement devices are electronically transmitted to a computer interface 16 and then to computer 17, e.g. an Apple II+ computer.

Figure 7:
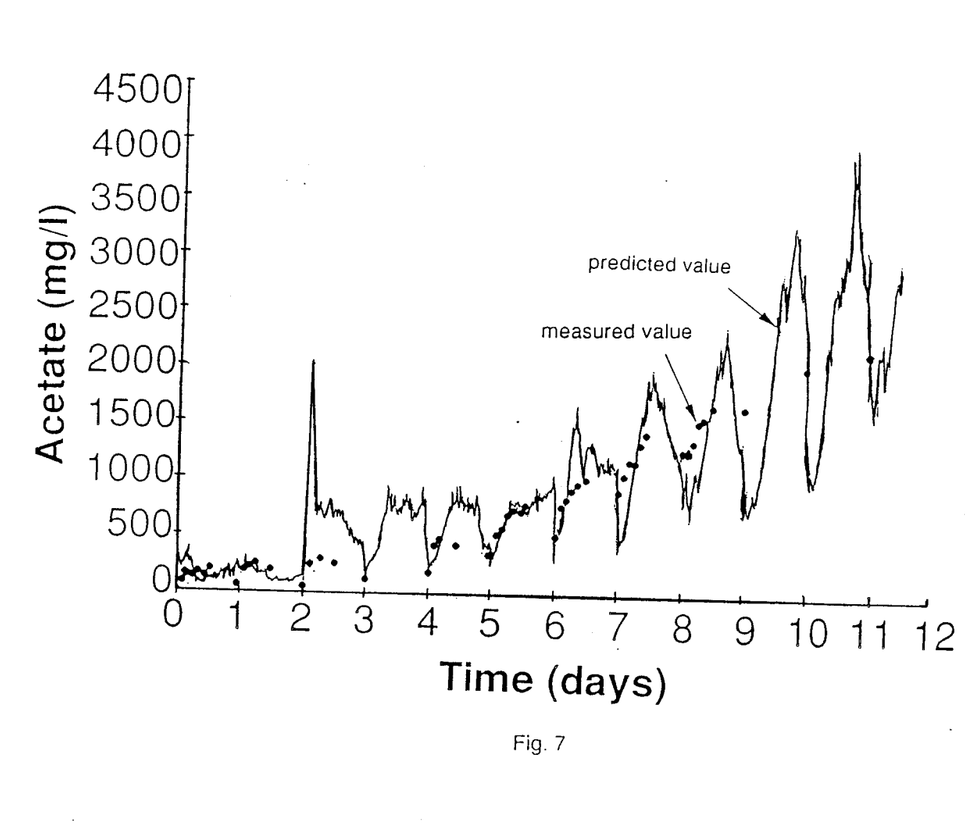
FIG. 7 is a plot of predicted acetate concentrations, derived from a thermodynamic model in accordance with the present invention versus measured acetate concentrations.

The results of the tests conducted with the discussed laboratory test equipment, will now be described with reference to FIG. 7. In FIG. 7, the predicted acetate concentrations, based upon the thermodynamic relationship presented as equation (7), is represented by the dotted line. These values were calculated using the headspace concentrations of CO, hydrogen, methane and carbon dioxide collected on a 15 minute interval basis with the on-line data acquisition system. The filled circles represent the measured acetate concentrations. These samples were collected manually and analyzed via gas-liquid chromotography. Note that although there is some difference between the predicted and measured values, the trends exhibited by the two are essentially the same.

It should be recognized that although all of the examples cited herein are for chemostat type reactors, the utility of this monitoring approach is not limited to such systems. The use of CO monitoring and/or process control for anaerobic fixed film systems such as anaerobic filters (AF), upflow anaerobic sludge blankets (USAB), anaerobic expanded/fluidized beds, anaerobic rotating biological contractors, hybrids of these process modifications as well as other novel process designs is possible. It will be understood by those skilled in the art that additional modification of the relationships presented herein may be necessary in these cases to account for the various hydraulic regimes and the mass transfer effects of substrate penetration into the biofilms (or granules) and diffusion of gaseous products and intermediates back out. These modifications do not diminish the usefulness of the invention but are necessary to properly evaluate the monitoring results.

Although headspace monitoring is the preferred technique for measuring CO and other gases of interest produced during anaerobic digestion, it is also possible to measure the concentration of these gases dissolved in the aqueous phase. The recent progress in the development and reliability of techniques such as membrane inlet mass spectrometry may make these approaches useful in monitoring the production of trace gases in the near future. The use of these techniques are considered to fall within the scope of this invention.

So too, the application of CO monitoring is not confined to engineered systems but may be useful in examining natural ecosystems such as anaerobic sediments or soil systems as well as process monitoring of in-situ groundwater and/or soil remediation techniques employing anaerobic treatment.

Still a further possible use of this invention would be to help detect the presence of anaerobic activity in difficult to monitor systems such as sediment/soil and-/or groundwater systems.

It will be evident also to those skilled in the art that the thermodynamic evaluation method used in conjunction with acetate conversion to methane is directly applicable to other biologically mediated or catalyzed processes. For example, development of a thermodynamic relationship for $N_2O$ in nitrification and denitrification processes and natural ecosystems may allow estimation of important parameters such as nitrate concentration. This is a significant improvement beyond the work of Saito et al. who used $N_2O$ production rate as a measure of solids or organic concentration. The thermodynamic relationship allows a much more accurate analysis to be made, for more diverse and variable conditions. In addition, the fact that concentration alone is required and not rate of production extends the utility of trace gas monitoring to systems such as sediments, soil systems and groundwater where accurate quantification of the volume of gas production (and therefore rate of production) is not feasible The use of other trace gases, integrally related to the metabolic activity of other biologically catalyzed reactions such as pharmaceuticals production will be obvious to those skilled in the art.

As mentioned, process control is also possible with this invention. A simple feedback control loop, which could be based upon the predicted acetate calculation, is schematically illustrated, as it might be applied to a laboratory test digester, in FIG. 6. In this case, the use of the thermodynamic relationship (equation (7)) is described for a system experiencing an organic overload. Gas concentration measurements for methane, carbon dioxide, hydrogen and CO obtained using detectors 10 and 12 are forwarded to the computer 17 through an appropriate interface device 16. The computer, is preprogrammed to calculate a predicted acetate concentration based upon the gas values and thermodynamic relationship (equation (7)) and compares this value to some preset limit. If the calculated acetate concentration does not exceed the preset limit, no action is taken. If the calculated acetate concentration does exceed the preset limit, the computer then sends a signal via the computer interface device 16 to stop the feed pump 7 from delivering more flow to the digester. When the calculated acetate level drops below the preset limit, the feed pump is restarted.

Although the control described above is a simple feedback type control loop, it would be obvious to those skilled in the art that more sophisticated control loops such as integral or proportional controls are possible options and considered to be within the scope of this invention. So too, the use of less sophisticated relationships such as the simple regression of equation (2) or even the measured concentration of CO alone can be used as the control parameter that is compared, to a preset limit to determine if a control action is required. Other control actions are possible and will be apparent to those skilled in the art.

From the foregoing, it will be apparent that a unique and effective method for monitoring and/or controlling biologically catalyzed processes has been developed which fulfills all of the objects previously set forth and represents a significant advance in this art.

Although specific illustrative embodiments of the invention have been described, it will be appreciated that various modifications, additions, substitutions and the like may be made without departing from the spirit of the invention, the scope of which is defined by the appended claims.

What is claimed is:

1. A method of monitoring a biologically catalyzed reaction, comprising the steps of:
   determining a trace gas which either is a metabolic intermediate produced during said reaction or equilibrates with a metabolic intermediate produced during said reaction;
   measuring the concentration of said trace gas evolving from said reaction; and
   using the concentration measurement to assess the metabolic status of the reaction via a deterministic relationship.

2. The method of claim 1 wherein said deterministic relationship comprises an empirical relationship describing said reaction.

3. The method of claim 1 wherein said deterministic relationship comprises a thermodynamic model of the reaction.

4. The method of claim 1 wherein the step of using the measured concentration to assess the metabolic status comprises employing the deterministic relationship to estimate the concentration of a different chemical component of interest for a particular application of the reaction.

5. The method of claim 4 wherein the different chemical component comprises one of: a reactant, a metabolite, and a product of the reaction.

6. The method of claim 1 further comprising the step of controlling the reaction in response to the assessment of the metabolic status of the reaction.

7. The method of claim 1 wherein said measuring step comprises collecting a sample of gases evolving from said reaction and then measuring the concentration of said trace gas in said sample.

8. The method of claim 7 wherein said sample is conditioned to remove moisture and particulate matter therefrom prior to the measurement of trace gas concentration.

9. The method of claim 1 wherein the concentration of at least one other gas involved in said reaction is measured and employed in the deterministic relationship.

10. The method of claim 1 wherein said reaction comprises an anaerobic digestion process.

11. The method of claim 10 wherein said anaerobic digestion process comprises methanogenesis and the trace gas comprises carbon monoxide.

12. The method of claim 11 further comprising the step of also measuring the concentration of hydrogen, methane and carbon dioxide evolving from said reaction; and
   wherein the step of using the measurement of trace gas concentration to assess metabolic status comprises estimating the concentration of acetate in accordance with the following thermodynamic relationship:

$$\text{acetate} = C^* \left(\frac{CO}{H_2}\right)^{d+1} *[(CH_4)/(CO_2)^d]$$

where acetate is measured in milligrams per liter, carbon monoxide (CO) is measured in parts per billion, hydrogen ($H_2$) is measured in parts per million, carbon dioxide ($CO_2$) is measured in atmospheres and methane ($CH_4$) is measured in atmospheres.

13. The method of claim 1 wherein:
   said deterministic relationship comprises a thermodynamic model of the reaction; the step of using the concentration measurement to assess the metabolic status comprises employing the deterministic relationship to estimate the concentration of a different chemical component of interest for a particular application of the reaction; the different chemical component comprises one of: a reactant, a metabolite, and a product of the reaction; said measuring step comprises collecting a sample of gases evolving from said reaction and then measuring the concentration of said trace gas in said sample; said sample is conditioned to remove moisture and particulate matter therefrom prior to the measurement of trace gas concentration; the concentration of at least one other gas involved in said reaction is measured and employed in the deterministic relationship; and further comprising the step of controlling the reaction in response to the assessment of the metabolic status of the reaction.

14. A method of monitoring a biologically catalyzed methanogenic process, comprising the steps of:
   measuring the concentration of carbon monoxide evolving from said process; and
   employing the measured concentration of carbon monoxide to evaluate the metabolic status of said process.

15. The method of claim 14 wherein the measured concentration of carbon monoxide is used to estimate the concentration of acetate in accordance with a deterministic relationship.

16. The method of claim 15 further comprising the step of measuring the concentration of hydrogen evolving from said process, and wherein said deterministic relationship has the following form:

$$\text{acetate} = A*\left(\frac{CO}{H_2}\right)^b$$

where acetate is measured in milligrams per liter, carbon monoxide (CO) is measured in parts per billion, hydrogen ($H_2$) is measured in parts per million and A, b are fitted regression coefficients.

17. The method of claim 15 wherein the concentration of hydrogen, methane and carbon dioxide evolving from said process are also measured and wherein said deterministic relationship comprises a thermodynamic model of the following form:

$$\text{acetate} = C*\left(\frac{CO}{H_2}\right)^{d+1}*[(CH_4)/(CO_2)^d]$$

18. A method for on-line monitoring of the condition of a biologically catalyzed system, comprising the steps of:
  monitoring the concentration of a trace gas produced in said system, said trace gas being related to the intrinsic metabolic status of organisms of interest within the system; and
  correlating the monitored concentration of the trace gas with one of a thermodynamic model and empirical relationship describing the system, to determine system status.

19. The method of claim 18, wherein the correlation step comprises employing the monitored concentration of the trace gas to estimate the concentration of a different chemical component of interest for a particular application of the system.

20. The method of claim 19 wherein the biologically catalyzed system is used for methanogenesis, the trace gas comprises carbon monoxide and the chemical component of interest comprises acetate.

* * * * *